United States Patent [19]

Kanisawa et al.

[11] Patent Number: 4,769,243
[45] Date of Patent: Sep. 6, 1988

[54] METHOD FOR PREPARING GREEN AROMA COMPOUNDS

[75] Inventors: Tsuneyoshi Kanisawa; Hideichi Itoh, both of Kanagawa, Japan

[73] Assignee: Takasago Perfumery Co., Ltd., Tokyo, Japan

[21] Appl. No.: 937,631

[22] Filed: Dec. 3, 1986

[30] Foreign Application Priority Data

Dec. 3, 1985 [JP] Japan ............................. 60-270701
Dec. 3, 1985 [JP] Japan ............................. 60-270702

[51] Int. Cl.$^4$ .............................................. A23L 1/20
[52] U.S. Cl. ........................................ 426/33; 426/35; 426/46; 426/51; 426/52; 426/634
[58] Field of Search ................. 426/33, 35, 46, 51, 426/52, 634, 656; 435/134

[56] References Cited

U.S. PATENT DOCUMENTS 3,220,851 11/1965 Rambaud ............................. 426/46
4,389,425 6/1983 Burr ..................................... 426/634
4,514,433 4/1985 Matsuura ........................... 426/634

*Primary Examiner*—Marianne Cintins
*Attorney, Agent, or Firm*—Sughrue, Mion, Zinn, Macpeak & Seas

[57] ABSTRACT

A method for preparing green aroma compounds is disclosed wherein raw soybeans are ground at a temperature of 60° C. or less, unsaturated fatty acid are added thereto form a mixture, and the mixture is stirred at a temperature of 5° to 60° C. while supplying air or oxygen to form green aroma compounds.

6 Claims, 5 Drawing Sheets

METHOD FOR PREPARING GREEN AROMA COMPOUNDS

FIELD OF THE INVENTION

The present invention relates to a method for preparing green aroma compounds, and more particularly to a method for preparing green aroma compounds which can impart a natural green aroma to perfumes and foods.

BACKGROUND OF THE INVENTION

Green aroma is widely present in fruits such as strawberries, bananas and apples, tree leaves, tea leaves and vegetables, etc., and plays an important role in aroma and taste. In the perfume industry reproduction of aroma or taste of natural products is an important subject. Thus, it is essential to utilize substances having the green aroma.

The main components of the green aroma are said to be aliphatic aldehydes and alcohols. At present chemically synthesized compounds such as n-hexanal, n-hexanol and hexene-3-ol are utilized. The green aroma in natural products is not represented by one or two synthetic substances, but is complicated. In order to obtain more natural green aroma, further research and development are necessary. In recent years health and fitness has gained popularity and it is increasingly desired to obtain flavors using only natural products which have been considered as safe. In regard to the green aroma, natural substances are required. However, there are few substances having an excellent green aroma. Therefore, development of such substances is now required.

Until now, investigations have concentrated on a method for removing soybean odor including green aroma during the processing of soybeans into foods. The present inventors have considered utilizing the mechanism of generation of green aroma in soybeans for the production of such aroma. That is, it was thought that in processing raw soybeans to produce soybean milk, if they were ground at low temperatures, their odor including green aroma would be generated and the milk would be inferior in quality, so, during the traditional processing the soybeans were ground at high temperatures which cause inactivation of enzymes in the soybeans. Therefore, investigations were not substantially made on how strong the green aroma was when it is generated while supplying air or oxygen.

The present inventors have found that the green aroma is generated when raw soybeans are ground in the presence of oxygen within the temperature range not causing inactivation of enzymes in the raw soybeans and then stirred in a fermentor while supplying air or oxygen. Further, they have found that the green aroma can be strengthened by adding higher unsaturated fatty acids which are considered to be precursors of the green aroma. Furthermore, it has been found that the green aroma components formed vary according to the types of fatty acids added. It has been confirmed that introduction of natural fats and oils as an unsaturated fatty acid source is effective in increasing the green aroma. It is considered that in the green aroma generation reaction lipase present in the soybeans participates, and it has been found that if lipase is added alone or together with the fatty acids, triglycerides in the fats and oils are positively decomposed and the formation of the green aroma component can be increased.

SUMMARY OF THE INVENTION

As a result of extensive investigations, it has been found that strong green aroma can be generated by adding unsaturated higher fatty acids and/or lipase to raw soybeans and utilizing the enzyme system in the raw soybeans, and that stronger green aroma can be generated by adding the fatty acids and lipase together.

Accordingly, an objective of the present invention is to provide a method for preparing inexpensively green aroma compounds which are safe and mild and are rich in natural properties.

The method for preparing green aroma compounds according to the present invention comprises grinding raw soybeans at a temperature of 60° C. or less, adding at least one of unsaturated fatty acids, fats and oils containing unsaturated fatty acids, and lipase to the ground product, and stirring the resulting mixture at a temperature of 60° C. or less while supplying air or oxygen.

DETAILED DESCRIPTION OF THE INVENTION

Figure 1:
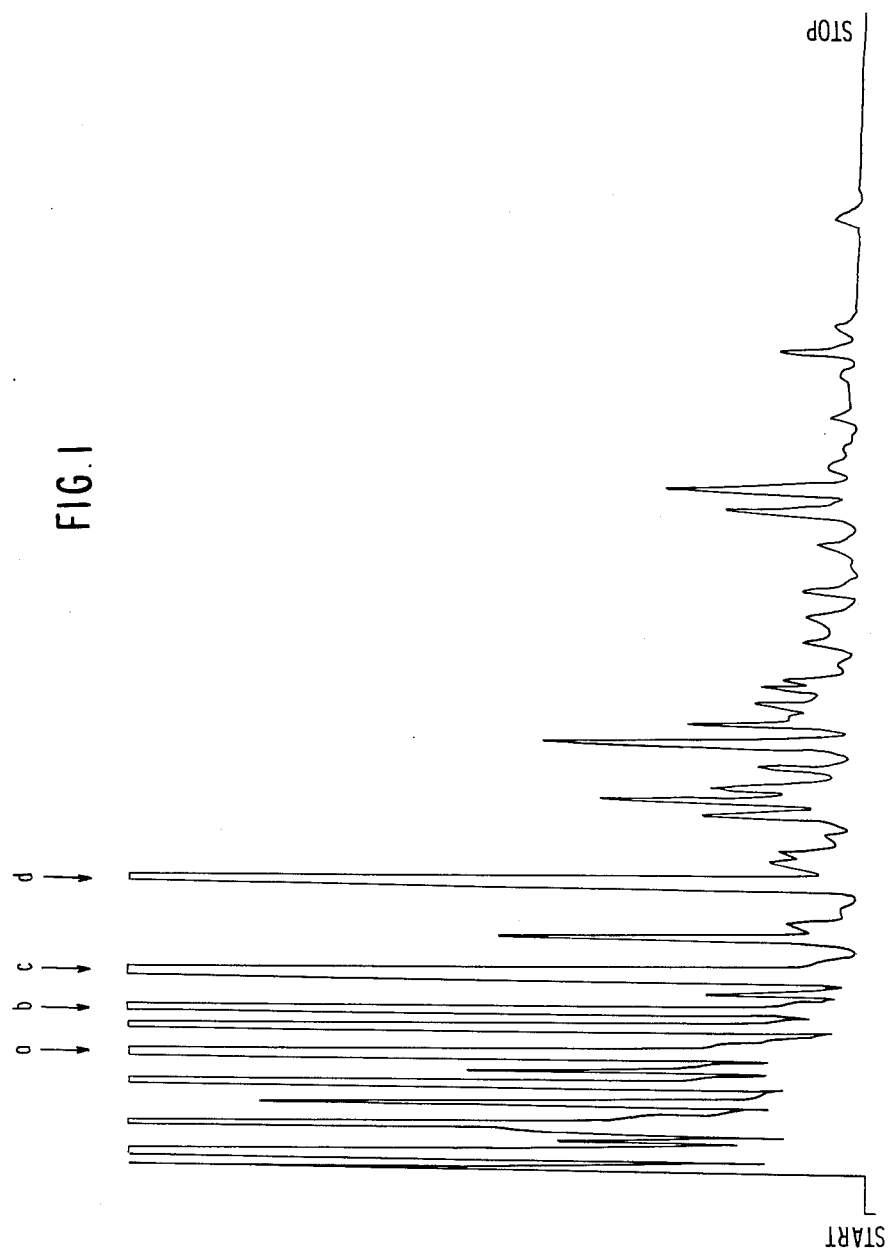
FIG. 1 is a gas chromatogram of green aroma compounds obtained in Example 1.

The raw soybeans which can be used in the method of the present invention can be any soybeans in which enzymes present therein are not inactivated, such as those not subjected to heat treatment. Soybeans with the skin removed have a green aroma-generating ability and the most suitable soybeans are of a round shape.

Grinding of the raw soybeans can be carried out by the conventional method. The grinding temperature should be set within the range in which enzymes present in the raw soybeans are not inactivated. In general, a suitable amount of water, preferably 3 to 20 times the weight of the raw soybeans, is added, and the resulting mixture is rapidly ground using, e.g., a waring blender, a colloid mill or a juicer. At this time, it is preferred from a standpoint of generation of aroma that the grinding is carried out in the presence of air or oxygen.

At least one of unsaturated fatty acids, fats and oils containing unsaturated fatty acids, and lipase is/are added to the above ground raw soybeans. These fatty acids, fats and oils, and lipase can be added prior to grinding, or during grinding, or after grinding of the raw soybeans.

The unsaturated fatty acids which can be used in the present invention become the precursor of the green aroma compounds, and usually are unsaturated higher fatty acids. Representative examples thereof are oleic acid, linoleic acid, α-linolenic acid, γ-linolenic acid, arachidonic acid, eicosapentaenoic acid and ricinoleic acid. Purity of these unsaturated higher fatty acids are not particularly limited. For example, a reagent class of fatty acids can be used, or products obtained by merely hydrolyzing fats and oils containing unsaturated fatty acids can be used. Of those fatty acids, particularly preferred fatty acids are oleic acid, linoleic acid and α-linolenic acid. For example, when oleic acid and linoleic acid are used, generation of n-hexanal in the green aroma component is increased. When α-linolenic acid is used, generation of 1-pentene-3-ol, trans-2-hexenal, cis-2-pentenol, etc., is increased. It is believed that this is due to the position of double bonds and the number of double bonds in the fatty acids.

Any kind of fats and oils such as plant fats and oils, animal fats and oils, and so forth can be used as the fats and oils in the present invention so long as they contain unsaturated fatty acids. Representative examples thereof are plant fats and oils such as soybean oil, linseed oil, safflower oil, olive oil, cacao butter, rapeseed oil, corn oil, tsubaki oil, groundnut oil, wheat oil, sesame oil, walnut oil, buckwheat oil, rice bran oil, castor oil, grape bean oil, palm oil and coconut oil; animal fats and oils such as milk butter, lard, cow oil, cod oil, herring oil, tuna oil, sardine oil, cuttle fish oil, mackerel oil, whale oil and turtle oil; and fats and oils produced by microorganisms.

The lipase which can be used in the method of the present invention has the function of releasing fatty acids from fats and oils. Any kind of lipase such as lipase originating from animals, lipase originating from vegetables, lipase originating from microorganisms, and the like can be used.

At least one of the unsaturated fatty acids, oils and fats, and lipase can be added in an appropriate amount.

Some of the unsaturated fatty acids and fats and oils have their own inherent odor and, therefore, the amount of these compounds used is determined such that their odor does not exert adverse influence on the final product and also the maximum green aroma can be generated.

Regarding lipase, a rapid effect is obtained as the amount of lipase added increases. However, it is generally sufficient that the amount of lipase added is from about several units to about several ten units per milliliter of the reaction solution.

The reaction for generating green aroma occurs under the enzymatic oxidative conditions. Therefore, it is preferred for the reaction to be carried out during vigorous stirring while air is being supplied (preferably sterile air) or oxygen.

The apparatus for conducting the reaction can be any type of apparatus if it satisfies the above requirements. An aeration agitation type fermentor is preferred.

The amount of the air or oxygen supplied is generally about 1/100 to 2 times the volume of the reaction solution per minute. If the amount of the air or oxygen supplied is too high, the green aroma compounds formed are lost. Therefore, it is preferred that the amount of the air or oxygen be 1/5 to ½ times the volume of the reaction solution per minute.

The reaction temperature should be set within the range in which the enzymes in the raw soybeans are not inactivated. The reaction temperature is generally 5° to 60° C. and preferably 25° to 50° C. The reaction is carried out until the green aroma compounds have been sufficiently formed. The reaction time is generally 5 minutes to 24 hours and preferably 30 minutes to 10 hours.

The homogenate thus obtained has a strong green aroma. This homogenate is subjected to heat treatment to inactivate the enzymes. The homogenate thus treated is used as a green aroma compound as it is, or is powdered by using, e.g., a spray drier and then used as powdery green aroma compounds.

The homogenate is distilled to obtain green aroma compounds and used as oil-soluble green aroma compounds, or a solvent such as ethanol or glycerine is added to the green aroma compounds obtained by distillation to make the oil-soluble fraction uniform, and the resulting solution is used as an essence type of green aroma compounds. The oily material obtained by distillation and the essence type of green aroma compounds are free of the flavor of soybeans other than the green aroma originating from the soybeans, and therefore can be effectively used as green aroma compounds for fruits.

The method of the present invention is a method wherein green aroma compounds can be obtained by a relatively simple procedure, and also produces relatively large amounts. In particular, in the case where lipase is used in combination with unsaturated fatty acids and/or oils and fats containing the unsaturated fatty acids, the amount of the aroma compounds formed can be increased (more than 3 times in the case of using unsaturated fatty acids and/or oils and fats containing the unsaturated fatty acids) by adding lipase. Furthermore, the method of the present invention is economical because relatively inexpensive soybeans are used as the raw material.

The green aroma compounds obtained by the method of the present invention have a natural green aroma rich in the natural properties. Therefore, it can be expected that they are used as a basic substances to be incorporated in various fragrances, and direct flavor-imparting substances.

As described above, the method of the present invention is useful in the fragrance and flavor industry, the food industry and the like.

The present invention is described in greater detail by reference to the following examples, which, however, are not exhaustive.

COMPARATIVE EXAMPLE 1

900 g of water was added to 100 g of raw soybeans. The mixture was vigorously ground for 4 minutes in a juicer, charged in a 3 liter minijar fermentor and then reacted with stirring at 1,000 rpm for 2 hours while supplying sterile air at a rate of 300 ml/min. The reaction solution thus obtained has a green aroma. This solution was distilled under atmospheric pressure to obtain 100 ml of a crude distillate. This distillate was then again distilled to obtain 20 ml of an initial fraction. A part of the initial fraction was analyzed by gas chromatography. This gas chromatogram is shown in FIG. 3.

COMPARATIVE EXAMPLE 2

20 ml of an initial fraction was obtained in the same manner as in Comparative Example 1 except that 900 g of hot water maintained at 98° C. was used in place of cold water (this initial fraction is hereinafter referred to as a hot-water-ground product). The liquid temperature after grinding was 75° C. A gas chromatogram of the initial fraction is shown in FIG. 4.

Figure 3:
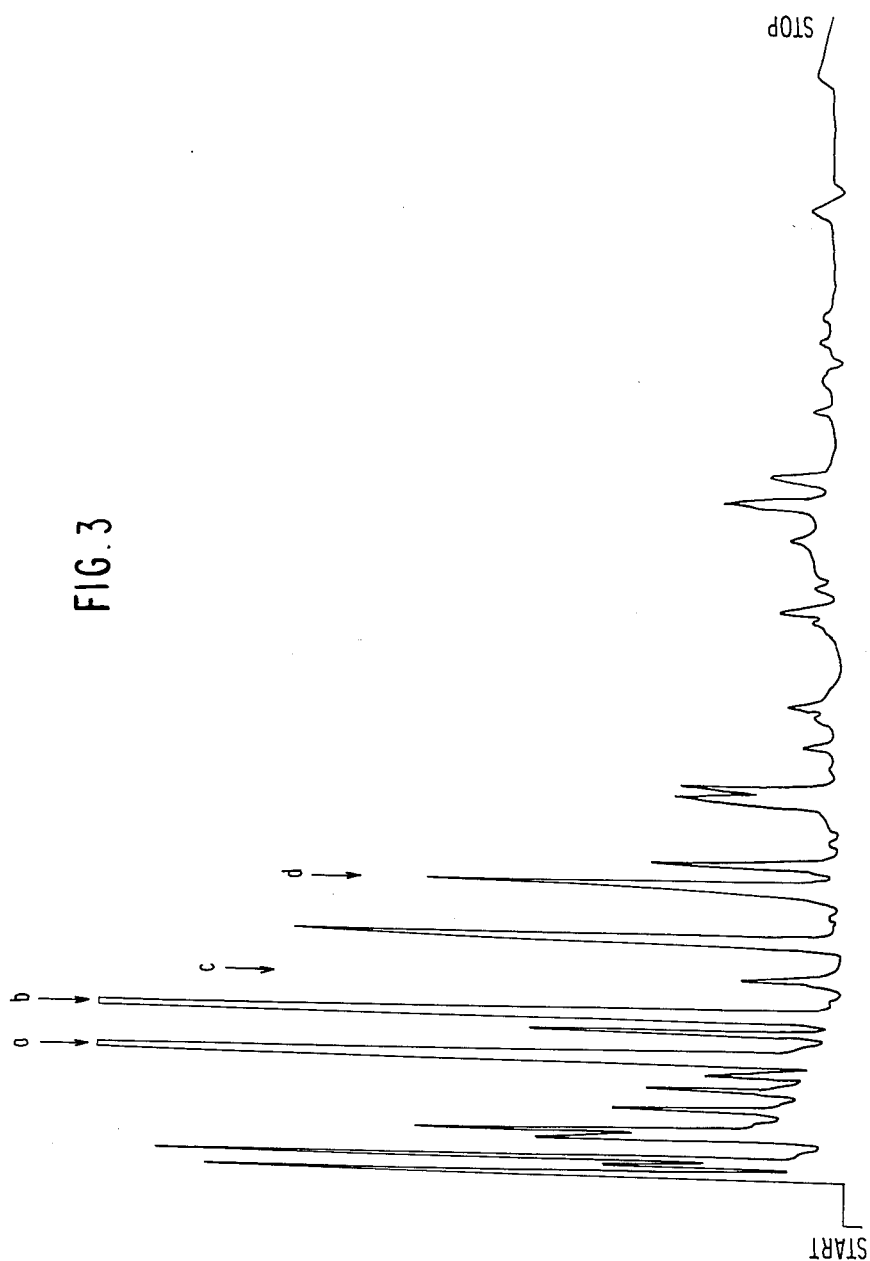
FIG. 3 is a gas chromatogram of aroma compounds obtained in Comparative Example 1.
Figure 4:
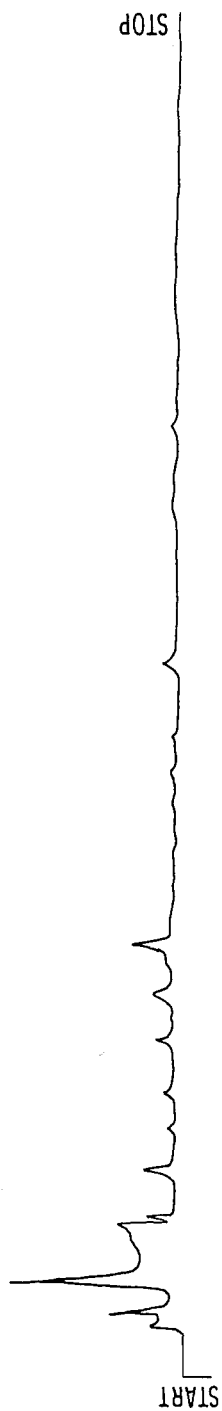
FIG. 4 is a gas chromatogram of a hot water ground product as obtained in Comparative Example 4.

It can be seen from the comparison of FIG. 4 with FIG. 3 that active enzymes participate due to the formation of green aroma compounds including n-hexanal. The ratio of the sum of aroma components was measured using a digital integrator. The amount of the aroma components formed in the hot-water-ground product was about 1/7 of that in Comparative Example 1.

EXAMPLE 1

1,350 g of water was added to 150 g of raw soybeans and vigorously ground for 4 minutes in a juicer. 30 g of linseed oil and 300 mg of lipase OF (produced by Meito Sangyo Co., Ltd.; 360,000 units/g) were added thereto, and the resulting mixture was charged in a 3 liter minijar fermentor and reacted for 2 hours while stirring at 1,000 rpm at 40° C. while supplying sterile air at a rate of 500 ml/min. The reaction solution obtained had a strong green aroma. This reaction solution was distilled under atmospheric pressure to obtain 150 ml of a crude distillate. This distillate was again distilled to obtain 30 ml of an initial fraction. A part of the initial fraction was analyzed by gas chromatography. This gas chromatogram is shown in FIG. 1. The sum of aroma components as measured by a digital integrator was about 77 times that of the aroma components of the hot-water-ground product of Comparative Example 2 (about 11 times that in Comparative Example 1).

The ratio of n-hexanal:1-pentene-3-ol:trans-2-hexenal:cis-2-pentenol which were main green aroma components was 3.7:3.4:2:1 and the compounds had green aroma in which the components were well balanced. The high proportion of the components other than n-hexanal are due to the fact that linseed oil contains a large amount of linolenic acid.

A flavor product having green aroma was prepared using the above initial fraction. That is, the separation of the oily substances was observed in the initial fraction since the amount of the aroma components was large and, therefore, 1 part by weight of glycerine was added to 1 part by weight of the initial fraction and stirred to dissolve the initial fraction. The green aroma material could be used effectively as a green aroma component for fruits flavors. A very strong aroma strength can be exhibited when the component is used at a concentration of about 1 to 10 ppm.

EXAMPLE 2

Figure 2:
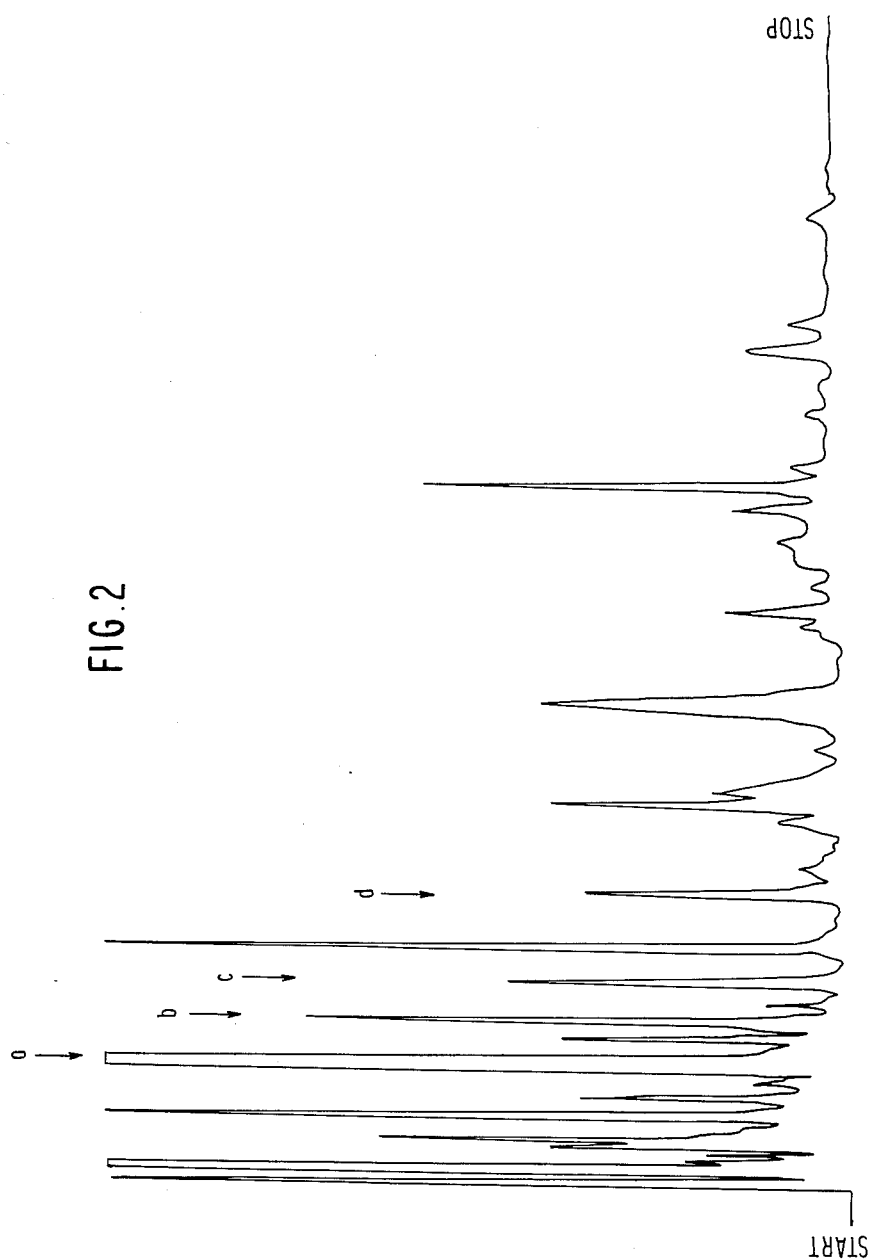
FIG. 2 is a gas chromatogram of green aroma compounds obtained in Example 2.

900 g of water, 20 g of safflower oil and 200 mg of lipase OF (same as in Example 1) were added to 100 g of raw soybeans and ground for 4 minutes using a juicer. The mixture was charged in a 3 liter minijar fermentor and reacted for 2 hours at 40° C. while stirring at 1,000 rpm and supplying sterile air at a rate of 300 ml/min. The reaction solution thus obtained was distilled under atmospheric pressure to obtain 100 ml of a crude distillate. This distillate was again distilled to obtain 20 ml of an initial fraction. A part of the initial fraction was analyzed by gas chromatography. This gas chromatogram is shown in FIG. 2. The ratio of the sum of aroma components as measured by a digital integrator was about 40 times that of the hot-water-ground product in Comparative Example 2. The ratio of green aroma components was such that n-hexanal:1-pentene-3-ol:trans-2-hexenal:cis2-pentenol was 38:1.6:1.3:1. The reason why the proportion of n-hexanal was markedly high is that the safflower oil contains a large amount of linoleic acid. The aroma quality is different from that in Example 1, which shows that the product can be used depending on the purpose of use.

EXAMPLE 3

900 g of water was added to 100 g of raw soybeans and ground for 4 minutes in a juicer. The mixture was charged in a 3 liter minijar fermentor, and 3 g of butter and 1 g of lipase 30 (produced by Scientific Protein Laboratories Co., Ltd., U.S.A.) were added thereto. The resulting mixture was further reacted for 3 hours while stirring at 40° C. at 1,000 rpm and supplying oxygen at a rate of 100 ml/min. The reaction solution thus obtained had a strong green aroma and low fatty acids odor. This reaction solution was distilled under atmospheric pressure to obtain 100 ml of a crude distillate. This distillate was again distilled to obtain 20 ml of an initial fraction. 20 g of glycerine was added to the initial fraction and stirred to dissolve the separated oil, thereby obtaining about 39.5 g of a product. This product could be used as a green aroma for milk products.

EXAMPLE 4

20 ml of an initial fraction was obtained in the same manner as in Example 2 except that 20 g of purified lard was used in place of the safflower oil and the reaction time was 3 hours. 20 g of glycerine was added thereto and stirred to obtain about 39.5 g of a product. This product could be used as a flavor material for meats.

EXAMPLE 5

The procedure of Example 2 was repeated with the exception that 10 g of linoleic acid was used in place of the safflower oil and lipase was not used. Gas chromatographic analysis showed that the contents of green aroma components such as 1-pentene-3-ol, trans-2-hexanal and cis-2-pentenol were high. The total of the aroma components formed was about 31 times that in the hot-water-ground product in Comparative Example 2.

EXAMPLE 6

The procedure of Example 2 was repeated with the exception that 20 g of linseed oil was used in place of the safflower oil and lipase was not used. Gas chromatographic analysis showed that the total of the aroma components was about 25 times that in the hot-water-ground product in Comparative Example 2. This product had a strong green aroma and could be used as a flavor material for fruits or tea.

EXAMPLE 7

18 kg of water was added to 2 kg of raw soybeans and continuously ground using a colloid mill. The mixture was charged in a 30 liter jar fermentor. 400 g of linseed oil, 200 g of oleic acid and 4 g of lipase OF (same as in Example 1) dissolved in a small amount of water were added thereto and the mixture was reacted for 3 hours while stirring at 40° C. at 500 rpm and supplying sterile air at a rate of 5 l/min. The reaction solution thus obtained was distilled under atmospheric pressure to obtain 3 liters of a crude distillate. This distillate was again distilled to obtain 1,000 ml of an initial fraction. Common salt was added to this fraction to sufficiently separate the aroma component. 18.5 g of an oily substance was obtained from the fraction. This product could be utilized as a basic substance in preparing fruit and vegetable flavor products.

EXAMPLE 8

Figure 5:
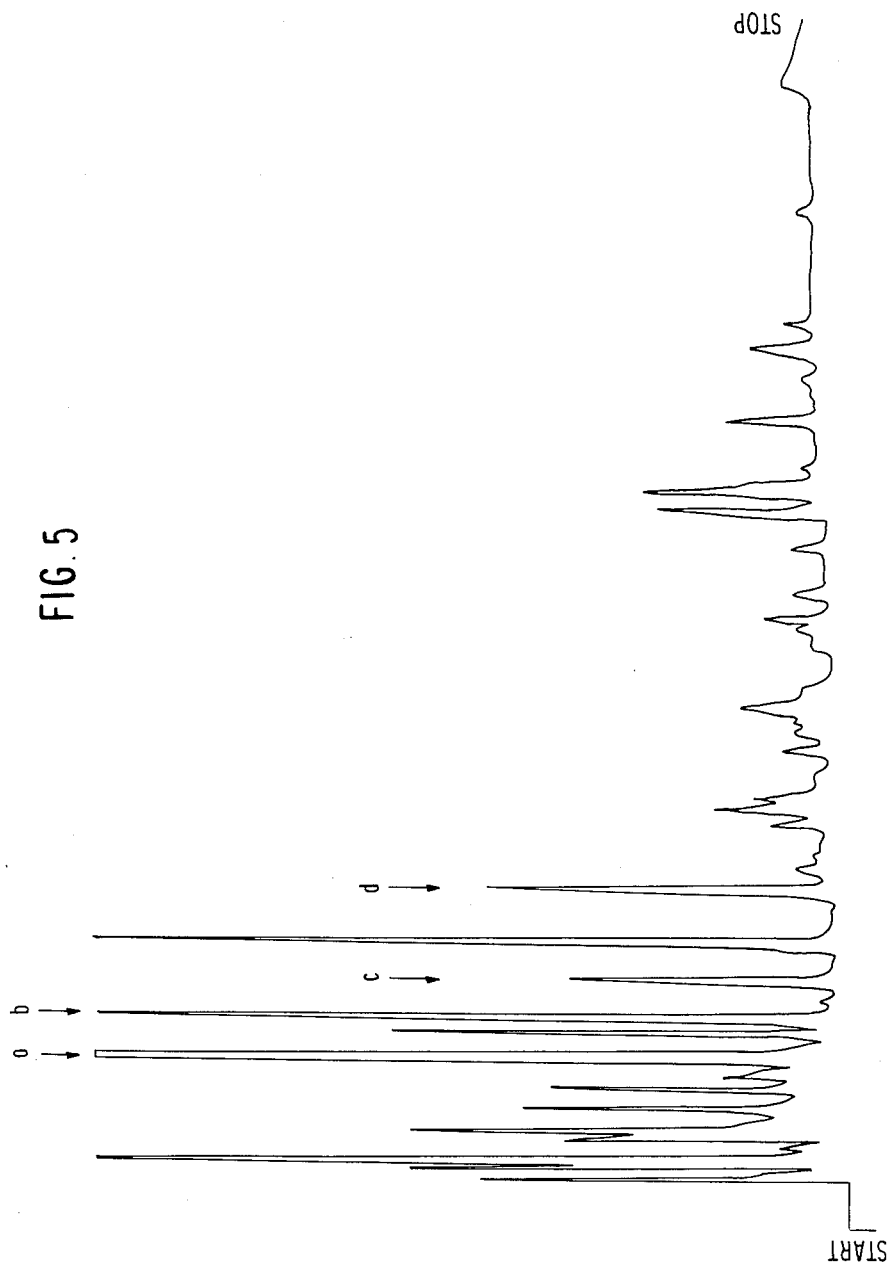
FIG. 5 is a gas chromatogram of green aroma compounds obtained in Example 8.

900 g of water was added to 100 g of raw soybeans and the mixture was ground vigorously for 4 minutes in a juicer. The resulting mixture was charged in a 3 liter minijar fermentor and 200 mg of lipase OF (same as in Example 1) was added thereto. The mixture was reacted for 2 hours while stirring at 1,000 rpm at 40° C. while supplying sterile air at a rate of 500 ml/min. The reaction solution obtained was distilled under atmospheric pressure to obtain 100 ml of a crude distillate. This distillate was again distilled to obtain 20 ml of an initial fraction. A part of the initial fraction was analyzed using gas chromatography. This gas chromatogram is shown in FIG. 5. The ratio of the sum of aroma components as measured by a digital integrator was about 3 times or more the aroma components as in Comparative Example 1 described above wherein lipase was not added and more than 22 times the aroma components of the hot-water-ground product of Comparative Example 2 described above.

2 g of the above initial distillate was weighed and 2 g of ethanol was added thereto. The mixture was stirred to obtain 4 g of an essence type green aroma product. This product contained a relatively large amount of n-hexanal and could be effectively utilized as a flavor substance for fruits.

EXAMPLE 9

850 g of water was added to 150 g of raw soybeans and the mixture was vigorously ground for 4 minutes in a juicer. The mixture was charged in a 3 liter minijar fermentor, and 1 g of lipase 30 (same as in Example 3) were added. The resulting mixture was reacted for 4 hours while stirring at 30° C. at 1,000 rpm and supplying oxygen at a rate of 100 ml/min. The reaction mixture was heat treated at 85° C. for 10 minutes and then spray dried to obtain about 120 g of a powder. This powder has a strong green aroma and could be utilized effectively as a powdery green aroma material.

While the invention has been described in detail and with reference to specific embodiments thereof, it will be apparent to one skilled in the art that various changes and modifications can be made therein without departing from the spirit and scope thereof.

What is claimed is:

1. A method of preparing green aroma compounds which comprises grinding raw soybeans in the presence of water at a temperature of 60° C. or less, adding to said ground soybeans unsaturated fatty acids to form a resulting mixture, said unsaturated fatty acids being present in an amount sufficient to strengthen the green aroma obtained from raw soybeans and stirring the resulting mixture for 5 minutes to 24 hours at a temperature of 5° C. to 60° C. while supplying a sufficient amount of air or oxygen to produce said green aroma compounds.

2. The method as claimed in claim 1, wherein the raw soybeans are of a round shape.

3. The method as claimed in claim 1, wherein the air is sterile air.

4. The method as claimed in claim 1, wherein the unsaturated fatty acids are selected from the group consisting of oleic acid, linoleic acid and linolenic acid.

5. The method as claimed in claim 1, wherein the unsaturated fatty acids are obtained from edible fats and oils having unsaturated fatty acids, said fats and oils being in admixture with lipase in an amount sufficient to release unsaturated fatty acids from said fats and oils.

6. The method as claimed in claim 5, wherein the fats and oils containing unsaturated fatty acids are selected from the group consisting of linseed oil, safflower oil, butter, purified lard, cod oil and castor oil.

* * * * *